United States Patent [19]
Rawls

[11] Patent Number: 6,017,334
[45] Date of Patent: Jan. 25, 2000

[54] MODIFIED SURFACES RESISTANT TO BACTERIAL COLONIZATION

[75] Inventor: H. Ralph Rawls, San Antonio, Tex.

[73] Assignee: Board of Regents, The University of Texas System, Austin, Tex.

[21] Appl. No.: 08/725,404

[22] Filed: Oct. 3, 1996

[51] Int. Cl.[7] .................................................. A61M 25/00
[52] U.S. Cl. ............................................................. 604/265
[58] Field of Search .................................... 106/15.05, 16; 623/1; 427/2.24, 2.25; 604/265

[56] References Cited

U.S. PATENT DOCUMENTS

| | | | |
|---|---|---|---|
| 3,106,483 | 10/1963 | Kline et al. | |
| 4,143,015 | 3/1979 | Soeterik | 106/15.05 |
| 4,306,563 | 12/1981 | Iwatschenko | 128/349 R |
| 4,315,505 | 2/1982 | Crandall et al. | 128/200.26 |
| 4,416,028 | 11/1983 | Eriksson et al. | 623/1 |
| 4,603,006 | 7/1986 | Sikes et al. | 427/384 |
| 4,654,380 | 3/1987 | Makepeace | 106/16 |
| 4,687,792 | 8/1987 | Russell et al. | 106/16 |
| 4,708,765 | 11/1987 | Newman et al. | 156/626 |
| 4,957,989 | 9/1990 | Saitoh | 526/279 |
| 5,004,631 | 4/1991 | Humphries et al. | 427/385.5 |
| 5,019,096 | 5/1991 | Fox, Jr. et al. | 623/1 |
| 5,049,139 | 9/1991 | Gilchrist | 604/265 |
| 5,096,488 | 3/1992 | Stovicek | 106/15.05 |
| 5,225,120 | 7/1993 | Graiver et al. | 264/28 |
| 5,269,770 | 12/1993 | Conway et al. | 604/265 |
| 5,429,839 | 7/1995 | Gravier et al. | 427/155 |
| 5,444,113 | 8/1995 | Sinclair et al. | 524/306 |
| 5,458,653 | 10/1995 | Davidson | 623/16 |
| 5,476,509 | 12/1995 | Keogh et al. | 623/1 |
| 5,494,660 | 2/1996 | Hunter et al. | 424/78.31 |
| 5,569,463 | 10/1996 | Helmus et al. | 427/2.12 |

OTHER PUBLICATIONS

Dankert et al., "Biomedical Polymers: Bacterial Adhesion, Colonization, and Infection," *CRC Critical Reviews in Biocompatibility,* 2(3):219–301, 1986 (no month).

Sheu et al., "A Glow Discharge Treatment to Immobilized Poly(ethylene Oxide)/Poly(propylene oxide) Surfactants for Wettable and Non–Fouling Biomaterials," *J Adhesion Sci Technol,* 6(9):995–1009, 1992 (no month).

van Wachem et al., "Interaction of Cultured Human Endothelial Cells with Polymeric Surfaces of Different Wettabilities," *Biomaterials,* 6:403–408, Nov. 1985.

*Primary Examiner*—Diana Dudash
*Attorney, Agent, or Firm*—Arnold, White & Durkee

[57] ABSTRACT

The present invention involves a surface having a coating consisting essentially of a polymer that is soluble in or hydrolyzable by water. When the surface is immersed in an aqueous medium, the coating slowly dissipates such that biological fouling of the surface is prevented or inhibited. Substances adhering to the surface of the slowly dissipating polymer are removed as the polymer dissipates. This dissipation may result from slow hydrolysis of the polymer, particularly if the polymer is a polyester or polyanhydride. Preferred polyesters include polylactide and polyglycolide. Polymers soluble in water include polyvinyl alcohol and polyethylene glycol. Such solubility must be sufficiently slow such that the surfaces may be coated and the water-soluble polymer remains for a long period of time and is slowly dissipated into solution. Such dissipation from the surface removes adherent substances. The adherent substances may be bacteria, fungi, biomolecules or multicellular organisms. The surfaces treated include polyvinylchloride, other plastics, elastomers, metals or ceramics.

15 Claims, 7 Drawing Sheets

MODIFIED SURFACES RESISTANT TO BACTERIAL COLONIZATION

BACKGROUND OF THE INVENTION

The present invention includes a method of preparing surfaces resistant to the accumulation of foreign substances and organisms, particularly when in contact with an aqueous system. Previously, various polymers have been irreversibly coupled to surfaces. Such coupled polymers had been thought to be resistant to the adherence, of various substances and micro-organisms. On occasion, various antibiotics were also coupled with or without such polymers to surfaces. The present invention, however, provides, for the first time, a method of coating surfaces with polymers that are slowly dissipated in an aqueous medium. Such slow dissipation carries any adherent materials, bacteria, fungi and other organisms away with the dissipating polymer and results in a surface that remains relatively free of biological fouling.

Dankert et al. have reviewed many aspects of biocompatibility, including resistance to bacteria adherence and biofouling.

SUMMARY OF THE INVENTION

The present invention involves a device having a surface having a coating consisting essentially of a polymer that is soluble in or hydrolyzable by water. When the coated surface is in contact with an aqueous medium, the coating slowly dissipates such that biological fouling of the surface is inhibited or prevented. Substances adhering to the surface of the slowly dissipating polymer are released as the polymer dissipates. Biological fouling, or biofouling refers to the attachment, accumulation or colonization by biomolecules and/or organisms.

The coated surfaces are preferably prepared by exposing the surface to a polymer solution. The solvent may be virtually any solvent for the polymer in use. A preferably coherent film of dissolved polymer is formed on the surface by, e.g, dipping, spraying or brushing. The solvent is then removed from the surface, preferably by evaporation. The procedure may be repeated to form as many polymer layers as desired.

The dissipation of polymer coatings may result from dissolution or hydrolysis of the polymer, e.g., into soluble fragments, particularly if the polymer is a poly-alpha-hydroxy-ester or a polyanhydride. Preferred polyesters include polylactide, polyglycolide and copolymers thereof. Other hydrolyzable polymers may include polyhydroxybutyric acid, polylactones, polyorthoesters, polyamino acids, chitin and other polysaccharide derivatives. Polymers sufficiently soluble in water include polyvinyl alcohol, polyvinylpyrolidone, cellulosics, including carboxymethyl cellulose, hydroxypropylcellulose and hydroxyethylcellulose, polyethylene oxide, polyethylene glycol, polypropylene glycol, polyglycerine, polyvinylmethyl ether, gelatine, alginate/alginic acid, agar-agar, polyacrylic acid, polyHEMA and their copolymers. Such solubility must be sufficiently slow such that the surfaces may be coated and the water-soluble polymer remains for a long period of time, e.g., for at least one day, while it is slowly dissipated into solution. Such dissipation from the surface removes adherent substances. The polymers are preferably noncovalently bound to the surface. However, covalent binding, particularly with hydrolyzable esters or anhydrides, is acceptable. The adherent substances that are prevented from accumulating on surfaces may be biomolecules, bacteria, yeast, fumgi, or other multicellular or unicellular organisms. The surfaces that can be treated include polyvinylchloride, other plastics, elastomers, composites, metals, wood, paper, glass or ceramics. The preferred coating has a thickness sufficient to substantially inhibit accumulation and biofouling in an aqueous medium for at least one day.

The coated surface, for example, may be that of a device immersable in or otherwise exposed to natural waters such as those, for example, of seas, rivers or lakes. In such cases the accumulaition of marine organisms is prevented or inhibited. Likewise such an immersable device may be one for containment of such waters such as, e.g., an aquarium or pipe. The surface may be that of medically implantable or indwelling devices in a body, such as a catheter, for example. Such a device is resistant to the accumulation of bacterial or biomolecule matter. Such coated devices may, after substantial coating dissipation, be removed from their emplacement dried and cleaned, if desired and then recoated.

The present invention includes a device or material used in contact with a biological fluid. This device has a surface at least partially coated with a polymer dissipating in the biological fluid. The portion of the surface coated is that portion contacting the biological fluid. The dissipation may involve hydrolysis of the polymer followed by dissolution or gradual dissolution of the polymer. Also included in the present invention is a device or material used in contact with marine water, coolant water or flushing/cleaning water. This device has a surface at least partially coated with a polymer dissipating in the water. The surface of the device in contact with the water is a surface coated with a polymer dissipating in the water.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF PREFERRED EMBODIMENTS

Figure 1:
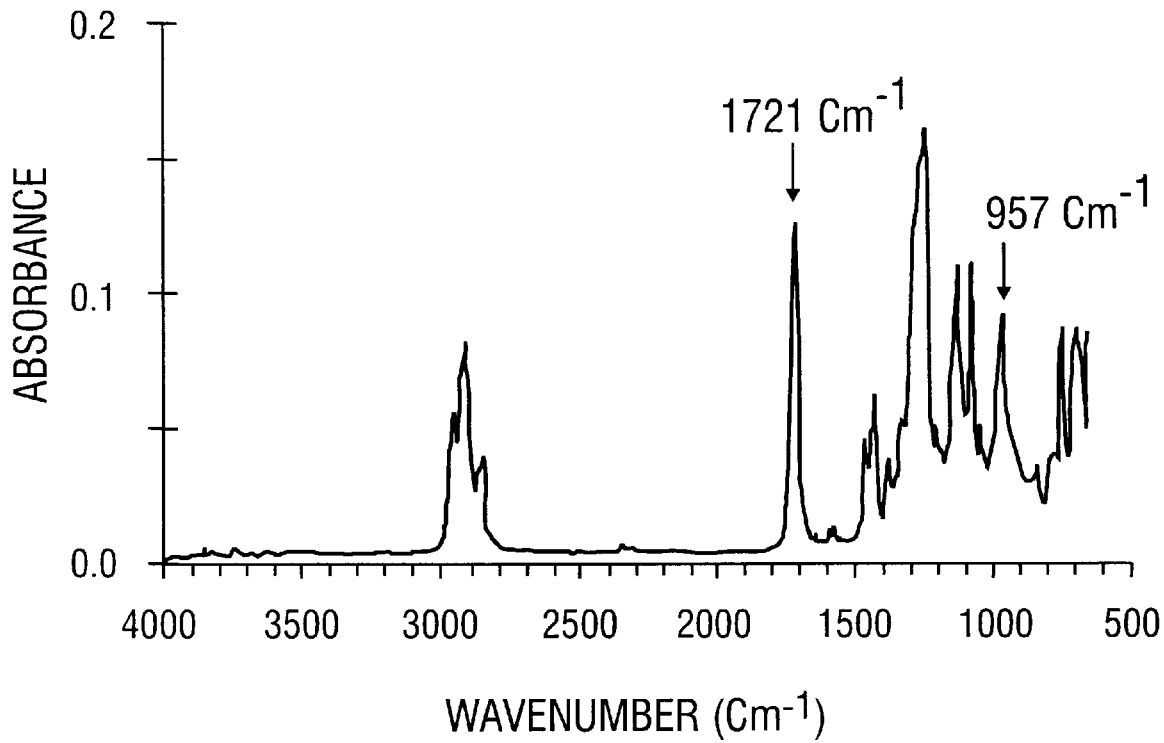
FIG. 1 shows the FTIR spectrum of uncoated PVC.

In the biomedical literature it is found that bacterial colonization of synthetic surfaces is a major cause of hospital-acquired infection. As long as the bacteria remain suspended ("planktonic") antibiotics are generally effective. However, once they attach to a surface they divide, form colonies and proliferate within an extracellular substance ("biofilm"). They are then largely unaffected by antibiotics. The present invention involves a synthetic material surface made to dissolve or degrade away—layer by layer at—at a rate fast enough to remove attached bacteria before they form colonies and a biofilm, but at a rate sufficiently slow so that the soluble/degradable surface would last long enough to be practical, then the synthetic material remains largely free of infective organisms. The basic problem in accomplishing this is to control the rate of loss of the surface material. Soluble or degradable polymer coatings offer this possibility. However, nothing in the technical or medical literature indicated that the rate of "self-cleaning" could be controlled well enough to prevent bacteria from accumulating faster than they could be removed by dissolution or degradation. Surprisingly, it was found that two representative types of polymers (soluble and degradable) were able to inhibit colonization, and that the efficiency of self-cleaning depended upon the molecular weight of the polymer. It was anticipated that the lower molecular weight (MW) polymers would be the most efficient, since polymers are generally known to dissolve or degrade faster as the MW decreases. However, it was found instead that the higher MW materials (both of the soluble and the degradable types) were more effective than the lower MW materials of the same type. This finding is useful because it indicates that the effective lifetime of a "self cleaning" coating will increase as its efficiency in preventing bacterial accumulation increases. The present invention concerns coatings rendering a surface resistant to fouling by biomolecules, cells and multicellular or unicellular organisms. Exemplary surfaces such as plastic, e.g., polyvinyl chloride may be rendered resistant to the accumulation and colonization of adherent microbial organisms. In addition to resistance to bacterial colonization, the prevention of biofilm formation or the accumulation of other organisms is also accomplished. Surfaces are coated with a polymer that is slowly soluble in and/or hydrolyzed by an aqueous solution or hydrolytic enzyme contained therein. Thus, as organisms or films adhere to the surface, the surface slowly dissipates taking any attached or adherent materials with it into the solution.

Polymer coatings may be slightly water soluble or at least only very slowly dissolved by aqueous solutions or in fact may be even subject to slow hydrolysis in an aqueous solution. Any polymer that has sufficient adherence to a surface to provide protection by these solubility characteristics, may be used. Preferred coatings include polyvinyl alcohol, agar-agar, alginate, soluble cellulosics such as, for example, carboxymethyl cellulose, hydroxypropylcellulose and hydroxyethylcellulose, polylactic acid, polyglyolic acid and their copolymers. Many other sufficiently soluble natural or synthetic gums and resins are known and could be used.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result with other surfaces and polymers without departing from the spirit and scope of the invention.

EXAMPLE 1

Polyvinyl Alcohol Coatings

Bacterial colonization of medical devices can be prevented by polymeric coatings that slowly dissolve in body fluids, thereby providing a self-cleaning surface that removes any attached bacteria or yeast. Polyvinylchloride (PVC) was chosen as a representative plastic substrate because it is a typical polymer used for medical tubing and other indwelling biomedical devices, and also as water line tubing in various medical, dental and other devices. PVC specimens were coated with polyvinylalcohol (PVA), a material that dissolves very slowly in water and is biocompatible. Three types of PVA coatings were used, a high molecular weight and a low molecular weight, and a mixture of the two. This produced coatings with three dissolution rates. Three coating thicknesses were prepared for each of the three types of PVA. The durability of the PVA coatings were determined by measuring the time required for the coating to dissolve in pH 7.4 phosphate buffer. The presence of the coating was followed using reflectance Fourier-Transform Infrared (FTIR) spectrometry. Specimens were also placed in a flowing stream of *S. epidermidis* in suspension in growth medium and the number of adherent colonies counted after six days exposure.

The coatings gradually dissolved but remained adhered to the PVC during dissolution. The lower molecular weight PVA was removed sooner than the others, and the thicker coatings lasted longer than the thinner coatings. The number of colonies were reduced to 14–54% of those observed on uncoated PVC, the reduction increasing with increasing PVA molecular weight. From these results, it was concluded that soluble PVA coatings can form a self-cleaning surface that resists bacterial colonization and that the longevity of the coating can be varied by the molecular weight and/or thickness of the coatings. This approach may be used for any biomedical material or device to which PVA can adhere and form a coherent film.

Intrusive medical devices such as catheters and endotracheal tubes are subject to microbial colonization and may, therefore, introduce infection into hospitalized or other patients. The most common source leading to colonization is the patient's skin, whereby organisms migrate from the skin along the intercutaneous catheter segment and ultimately enter the bloodstream where they can create serious infections. The most common organisms causing these infectious complications are *Staphylococcus epiderimidis* and *Staphylococcus aureus*. In the case of vascular catheters, these two organisms account for almost 80% of all infectious organisms, with *S. epidermidis* being the most common. *Candida albicans* accounts for about 15% of catheter infections. A number of studies have revealed that organisms such as *S. epidermidis* attach by sending projections into small defects in the catheter surfaces. Following attachment, colonization is established and an extracellular biofilm is produced. The biofilm provides a protective environment so that the bacteria colonies become highly resistant to antibiotics and other means of elimination.

The present example shows that one or more soluble polymer layers applied to the surfaces of biomedical devices slowly dissolve and act to form a self-cleaning surface, removing any adherent bacteria before colonization could be established. Such a coating preferably also meets at least two additional criteria: it should not contribute any harmful effects and it should adhere to the substrate material and remain adhered even as at least part of it dissolves.

Polyvinylchloride (PVC) is a representative plastic substrate and polyvinylalcohol (PVA) a representative coating material that has desirable properties. Plasticized PVC is commonly used in endotracheal tubing and catheters, and is a component in a number of other medical devices. As a biomedical material, it is readily colonized by opportunistic microorganisms. PVA is a water soluble polymer, it is biocompatible, available in a range of molecular weights, and is approved for a variety of food, drug and cosmetic applications. Since PVA solubility decreases as its molecular weight (MW) increases, variation of MW provides a means of controlling the rate of self-cleaning and coating longevity. PVA also provides a second possible protective mechanism: a high equilibrium water content. Being very hydrophilic, PVA swells and absorbs about 80% water prior to dissolution. A high equilibrium water content, plus a high level of intrachain motion, may contribute to the ability of a surface layer of polyethylene oxide to prevent cellular and bacterial attachment (van Wachen et al., 1985; Sheu et al., 1992). A swollen outer PVA coating layer could well provide a similar effect.

The procedure was carried out in three stages: development of a coating technique, testing coatings to verify dissolution and durability in a body fluid-like environment, and exposure to bacterial culture to determine resistance to colonization. PVC disks were prepared, coated with PVA and the time required for removal in an agitated pH 7.4 buffer was determined using reflectance Fourier-transform IR spectroscopy (FTIR). Resistance to bacterial colonization was then evaluated using a continuous culture (chemostat) suspension of S. epidermidis in a flow-contact fixture (modified Robbins device).

Polyvinyl chloride disks: Two disk sizes were prepared: 25 mm diameter for the dissolution measurements and 7.8 mm diamneter for the bacterial colonization experiments. For the dissolution experiments PVC (plasticized with 25% diethylhexylpthalate) was molded into disk-shaped specimens in a hydraulic press. Approximately 1.5 g of PVC pellets (obtained from Mallinckrodt Medical, Inc., St. Louis, Mo.) were heated for 22 min at a line pressure of 83 psi and a ram pressure of 70 psi. No facility was available to measure the molding temperature but it is estimated that it was well above 150° C. The finished specimens were 25 mm diameter and 1.4 mm thick. For the bacterial colonization specimens, the same procedure was used except that the heating time was decreased to 18 min. This resulted in a thickness of 1.8 mm. A mechanical cork borer was used to punch out 6–7 disks of 7.8 mm diameter from each 25 mm disk. FIG. 1 shows a FTIR spectrum of PVC.

Figure 2:
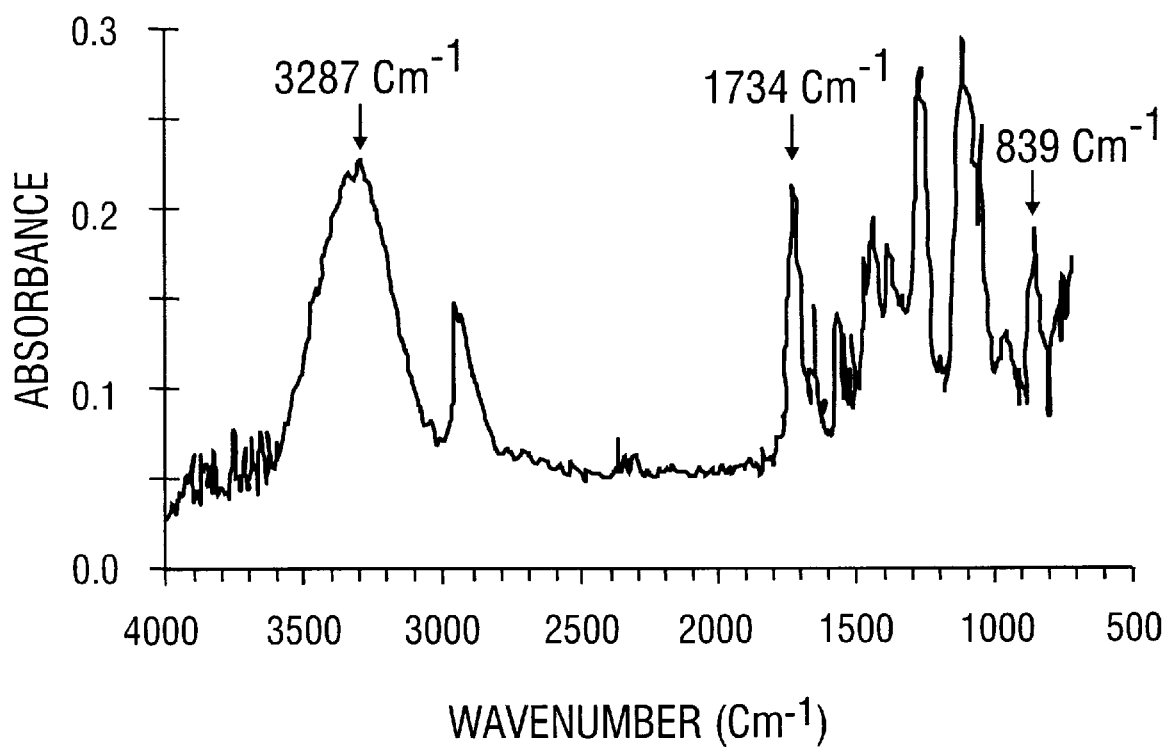
FIG. 2 shows the FTIR spectrum of PVA.

Polyvinyl alcohol coatings: The higher the MW, the longer it takes for PVA to dissolve. Therefore coating solutions using a high and a low molecular weight PVA, and one with an intermediate MW prepared by a 1:3 mixture of the other two, were prepared. ELVANOL® polymers, a series of commercial PVA materials supplied by Du Pont Polymers, Wilmington, DE, were used. The relative viscosity, but not MW, and degree of hydrolysis are given by the manufacturer for these materials as follows: ELVANOL 50-42, high viscosity (44-50 cP, 4% solids), 87–89% hydrolyzed from polyvinylacetate; ELVANOL 51-05, low viscosity (5-6 cP, 4% solids), 87–89% hydrolyzed. FIG. 2 shows the FTIR spectrum of PVA.

To make the coating solutions, PVA powder was placed in water at 80–85° C., stirred until no cloudiness could be detected, and then diluted with an equal volume of ethanol. The three solutions were diluted with sufficient of the mixed solvent to produce equal viscosities rather than equal concentrations. Thus, the lower MW solution was diluted the least (to 5%) and the higher MW solution was diluted the most (to 3%). The intermediate-viscosity solution was prepared from 2% 50–42 and 6% 51–05. Equal viscosity solutions are expected to produce approximately equal coating thicknesses when using a dip-coating technique.

Figure 3:
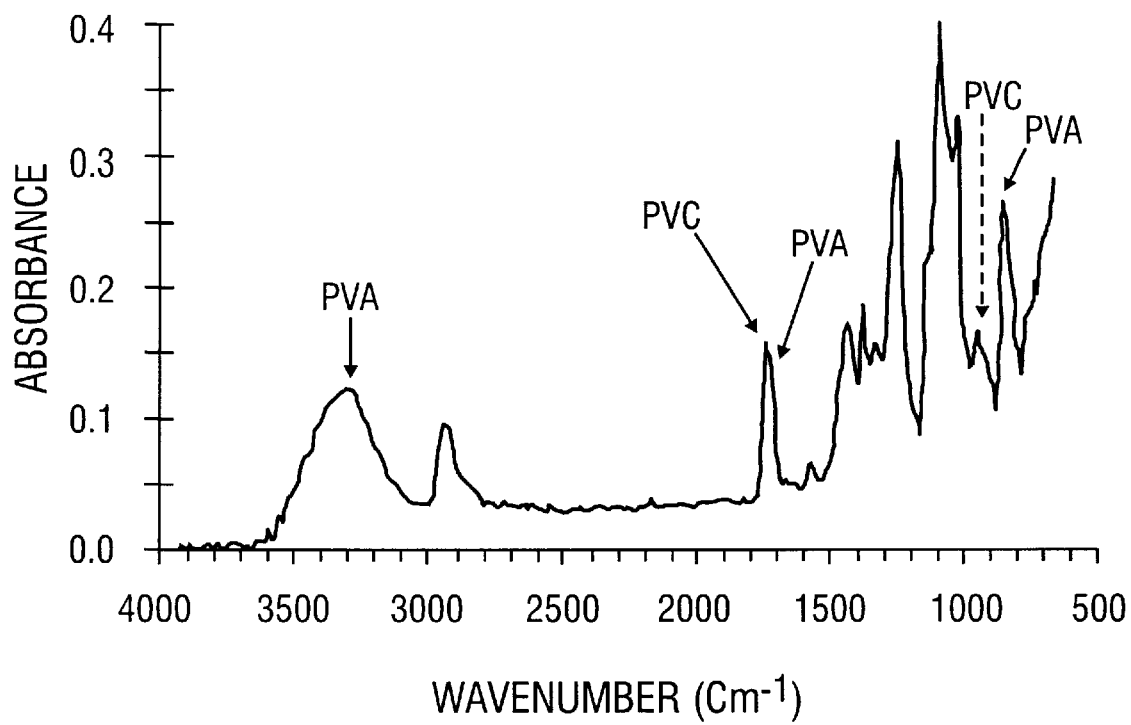
FIG. 3 shows the FTIR spectrum of PVC coated with PVA.

The PVA was applied in thin layers by submerging up to six disks at a time for 15 sec. They were then allowed to dry in air for about 30 sec before placing in a desiccator for 24–72 hr to remove all solvent. The specimens scheduled for bacterial colonization testing were placed directly in the vacuum desiccator to minimize the chance of contamination. All specimens were placed with the side to be tested facing upwards and all handling was done with sterile forceps. For increased coating thickness, the procedure was repeated a second or third time (1, 2 or 3 dips with complete drying in between). Two specimens were prepared for each coating thickness for the dissolution/durability studies and ten specimens of a single-dip thickness were prepared for the bacterial colonization studies. FIG. 3 shows the FTIR spectrum of PVC with a PVA coating.

Coating durability: Each specimen was placed in 30 mL of pH 7.4 phosphate buffer and agitated in a shaker bath at 25° C. for various intervals. Prior to beginning and at each interval, specimens were dried for at least 24 hr in a vacuum desiccator and the presence of the coating was determined using reflectance FTIR spectroscope (0.5 cm$^{-1}$ spectrometer, Midac Corp., Costa Mesa, Calif.; ZnSe prism liquid cell PLC-11M, Harrick Scientific, Ossining, N.Y.). With this method the specimen is clamped against a ZnSe (zinc selenide) prism and the IR beam passes through the prism and is reflected from the specimen's surface, after penetrating a few microns into it. When the coating is thicker than the beam's penetration path, only the coating is detected. After the coating has decreased to less than the beam penetration path, the substrate material (plasticized PVC in the inventor's case) is detected together with the coating. Before the coating is applied or after it has been removed, only the PVC is detected.

Resistance to bacterial colonization: Coated and non-coated specimens were exposed to a flowing suspension of S. epidermidis in a flow-through "Robbins" device in which the specimen surface faces downward, eliminating any bacteria accumulation from simple settling. A chemostat (Bioflo benchtop model C30, New Brunswick Scientific Co., Edison, N.J.) was used to culture S. epidermidis RP62A (American Type Culture collection 35984) in a dynamic, chemically-defined growth medium. After steady-state growth was reached ($T_D$=14 h) the culture was pumped through the flow-through fixture at about 0.5 mL/min for six days. Up to 50 specimens were exposed in each test run. After six days exposure, one specimen representing each type of coating was examined by scanning electron microscopy. The other specimens were used to determine the number of viable bacteria colonies, after three and six days exposure, using a serial dilution/agar overlay procedure.

Coating longevity: The FTIR spectrum of uncoated PVC (see FIG. 1) showed absorption peaks characteristic of the plasticizer diethylhexylpthalate (DHEP), at 1721 cm$^{-1}$ and 957 cm$^{-1}$, which do not overlap with PVA peaks. They were therefore used to identify plasticized PVC. The coated specimens showed characteristic peaks at 3287 cm$^{-1}$, 1734 cm$^{-1}$ and 839 cm$^{-1}$ which could be used to identify polyvinylalcohol (see FIGS. 2 and 3). The spectra of the three types of PVA were identical.

The coatings completely obscured the spectrum of the underlying PVC and showed only the spectrum of PVA. As time in the buffer solutions increased, the PVA peaks were at first unaffected. Eventually, however, the DEHP/PVC peaks appeared and gradually increased in intensity relative to the PVA peaks. These results are illustrated by FIG. 1, FIG. 2 and FIG. 3. It was observed that the PVA spectrum disappeared after a shorter time for the lower MW coating (ELVANOL® 51-05), compared to the higher MW coating (ELVANOL® 50-42). In all specimens the time required for the DEHP/PVC peaks to appear was much greater than the six days used in the bacterial colonization studies.

Figure 4:
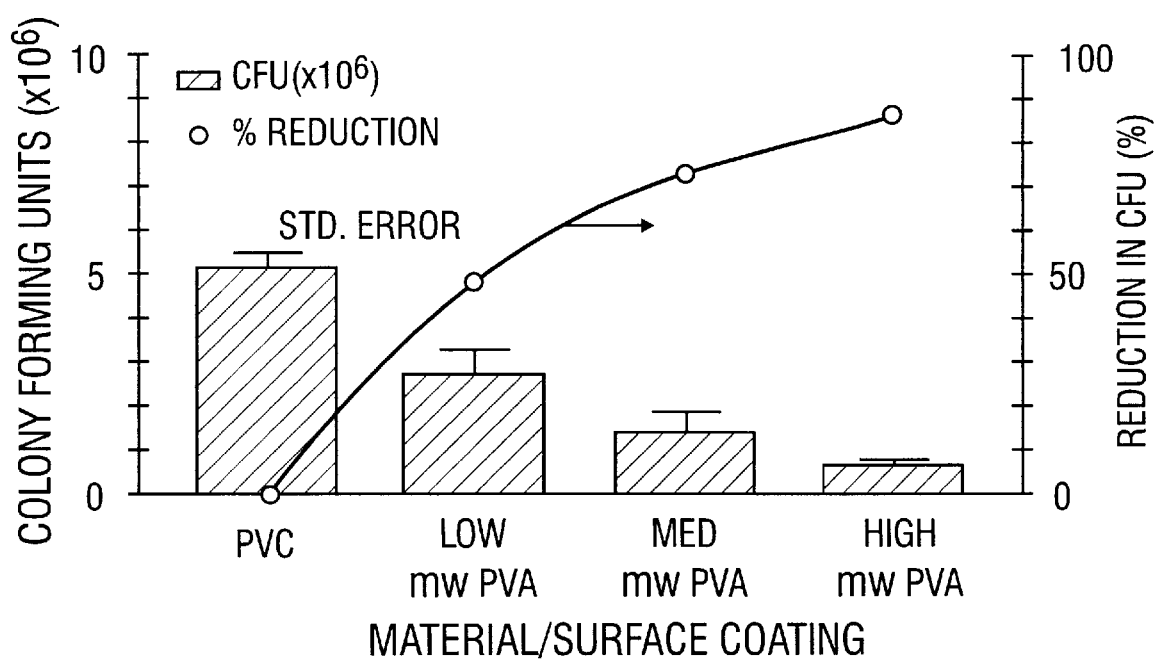
FIG. 4 shows the inhibition of bacterial colonization on PVC by various PVA coatings.

Resistance to bacterial colonization: Colony forming units (CFU) decreased in the order—$5.1 \times 10^6$ (uncoated PVC), $2.7 \times 10^6$ (low MW PVA coating), $1.4 \times 10^6$ (51-05/50-42 PVA mixture), $0.7 \times 10^6$ (high MW PVA coating). These results indicate reductions in colony counts ranging from 48 to 86%: low MW, ELVANOL® 51-05, 48%; intermediate MW, 51-05/50-42 mixture, 73%; high MW, ELVANOL® 50-42, 86%. These results are illustrated in FIG. 4.

From the results of the dissolution/durability studies, it is clear that the coatings slowly dissolve and that the rate is dependent upon the molecular weight of the PVA. Also, the coatings remained intact and did not become detached even though they became water swollen and slowly dissolved. Changes in coating thickness could not be measured using the FTIR technique. However, the observation that PVA peaks initially masked the DEHP/PVC peaks, and later gradually disappeared after the DEHP/PVC peaks reappeared, is evidence that the PVA coatings dissolved from the outer surface and thereby maintain a self-cleaning surface.

The bacteriological studies demonstrated that, indeed, PVA coatings substantially and significantly reduced colonization by *S. epidermidis*, and that the reduction increased as PVA molecular weight increased. It is apparent that a slowly dissolving coating removed adherent bacteria and prevented colonization. A contributing mechanism could involve the high equilibrium water content (EWC) of the swollen PVA coatings. A high EWC has been shown to be one of the factors that account for the inhibiting effect of polyethylene oxide, polyethylene glycol and other polymers on protein adsorption and bacterial, cell and platelet adhesion on biomaterial surfaces (Dankert et al., 1986).

EXAMPLE 2

Polylactic Acid Coatings

A further surface modification technique was developed in order to prevent and reduce bacterial colonization on polyvinylchloride (PVC). The PVC was coated with a biodegradable material, polylactic acid (PLA), using three different molecular weights. The PLA coating was then tested for longevity using a buffer solution, and surface composition changes were characterized using a Fourier-Transform Infrared (FTIR) spectrometer. The results indicated that the coating gradually degraded, and the rate of degradation was determined by the molecular weight. Initial bacteriological testing indicated that the biodegradable PLA resulted in reduced bacterial colonization. The PLA molecular weight influenced the mechanism of bacterial colonization.

The prolonged use of prosthetic medical devices has long been associated with mild to life threatening bacterial infections. *Staphylococcus epidermidis*, a part of the normal and non-pathogenic bacterial flora, has been linked as a common cause of these biomaterial-associated infections. Initial colonization by the bacteria leads to production of a biofilm that enables rapid multiplication and formation of macrocolonies. Once the biofilm is established on the biomaterial, bacteria become highly resistant to elimination.

Among the various types of medical tubing, a major component is polyvinylchloride (PVC). Polylactic acid (PLA) was used to coat PVC surfaces as a means of preventing or reducing bacterial colonization. PLA was chosen due to its nontoxicity and ease of degradation to form lactic acid. When the coated PVC is placed in vivo, the bacteria should colonize on the surface of the PLA. The PLA in contact with aqueous media will hydrolyze and hence remove any attached bacteria, maintaining a surface free of opportunistic pathogens. A contributing mechanism, indicated by early bacteriological testing, is that upon hydrolysis, PLA forms lactic acid. Consequently, at the immediate surface of the PVC, acidic conditions may inhibit the growth of *S. epidermidis* or other microorganisms.

In order for the PLA coatings to be used on medical devices it preferably serves a two-fold purpose: resist bacterial colonization and remain effective for long incubation periods in contact with biological fluids. To test these factors, PLA-coated samples were tested for their longevity in a buffer solution and for their inhibitory potential by exposure to bacteria cultures.

Polyvinylchloride (PVC) discs were coated with polylactic acid (PLA) and tested for both coating longevity and resistance to bacterial colonization. The longevity testing involved exposure of the coated PVC to a buffer solution, which simulated body fluids, for varying increments of time. Resistance to colonization was evaluated by exposure of the specimens in a flow chamber to suspension of *S. epidermidis*.

Polyvinylchloride (PVC) Disks: Since the samples were to be analyzed in an FTIR spectrometer, they were specially prepared for use on a reflectance prism. The samples had to make intimate contact with the prism surface and cover the entire area in order to maximize the spectrum quality. The procedure consisted of weighing out 1.5g of PVC pellets which were then placed in a pneumatic press and heated for 22 min at a line pressure of 83 psi and a ram pressure of 70 psi. This was immediately followed by a 30 min cooling period. The resulting samples measured approximately 25.0 mm in diameter and 1.4 mm in height.

PVC samples were also tested for resistance to bacterial colonization using a chemostat and a regulated flow system to expose specimens to bacterial suspensions. Thus, the preparation method for the PVC samples was altered to provide the diameter and height needed for use in the chemostat. The heating time in the pneumatic press was reduced to 18 min, while the pressure and temperature settings were held constant. The samples were then punched out from the 25 mm disk using a mechanical bore. The discs were 7.8 mm in diameter and 1.8 mm in height.

Polylactic Acid (PLA) Solution: It is known that the higher the molecular weight of PLA, the longer it takes to fully degrade. To determine if degradation rate would affect colonization, PVC samples were coated with PLA of three molecular weights: 2000, 300,000, and 700,000 (Polysciences). The PLA was dissolved into solution and then coated onto the samples. The solvent used was selected based on two criteria: a) high rate of evaporation (to facilitate rapid drying to form a coating) and b) high solubility for PLA. Methylene chloride fulfilled both criteria. The three molecular weight PLA versions were prepared in concentrations adjusted to provide solutions of equal viscosities rather than equal concentrations. Viscosity was measured using a flow rate measurement technique. Equal viscosity solutions should lead to approximately equal coating thickness when using a dip-coating technique.

PLA Coating of PVC: The coating of the PVC discs with the PLA was done using a dip-coat method. The PVC samples were dipped in the PLA solution for a maximum of 15 sec. As the PLA dried on the surface of the PVC, the sample was gently moved back and forth to promote even coverage. Finally, after air drying for 1 min, the coated specimens were placed in a vacuum desiccator for 24 hr.

Although the general coating procedure was the same, the bacterial resistance testing required a different approach. The samples had to be coated in a manner that minimized the possibility of bacterial contamination. Hence skin, surface, and air exposure were minimized. The samples were dipped in the PLA solution for 15 sec and then immediately vacuum desiccated, reducing the air exposure time. The samples were placed in the desiccator with the side to be tested facing upwards. This helped to reduce surface contact in the desiccator. All handling of the samples was done using sterile forceps.

Longevity Testing: The longevity of the PLA coating was tested in a phosphate buffer solution (~7.4 pH). The buffer solution simulated biological conditions in the body. The samples to be tested were placed in 30 ml of buffer and then in a shaker/stirrer for various incremental intervals at room temperature (~25° C.). Samples were then dried, after each interval, for a minimum of 24 hr in the vacuum desiccator. Once the sample was dry the surface coating was tested for variations in compositions and thickness with a Midac Fourier-Transform Infrared (FTIR) spectrometer using the attenuated total reflectance (ATR) method. The samples were placed in intimate contact with a germanium ATR prism by means of a thumb-screw clamp. In this method an infrared beam is reflected from the specimen surface, but penetrates a few microns below the surface. Thus, the reflected spectrum recorded in the spectrometer represents only the surfaces of the specimens. An FTIR spectrum was taken before coating, after coating and after each interval in the buffer solution. In addition, spectral analysis was also done for pure PLA. This information was used in determining relative rates of degradation for PLA and its different molecular weight forms.

Bacteriological Testing: The susceptibility of coated and non coated PVC specimens to bacterial colonization was determined using a specially modified chemostat. This apparatus provided a dynamic growth environment in which coated samples were placed face-down in contact with a flowing suspension of *S. epidermidis* in growth medium. Thus, the micro-organisms had the opportunity to attach but not settle on the surfaces. Resistance to bacterial attachment and colonization was determined by colony counting after six days exposure and by scanning electron microscopy (SEM) after three and six days of exposure.

RESULTS

Figure 5:
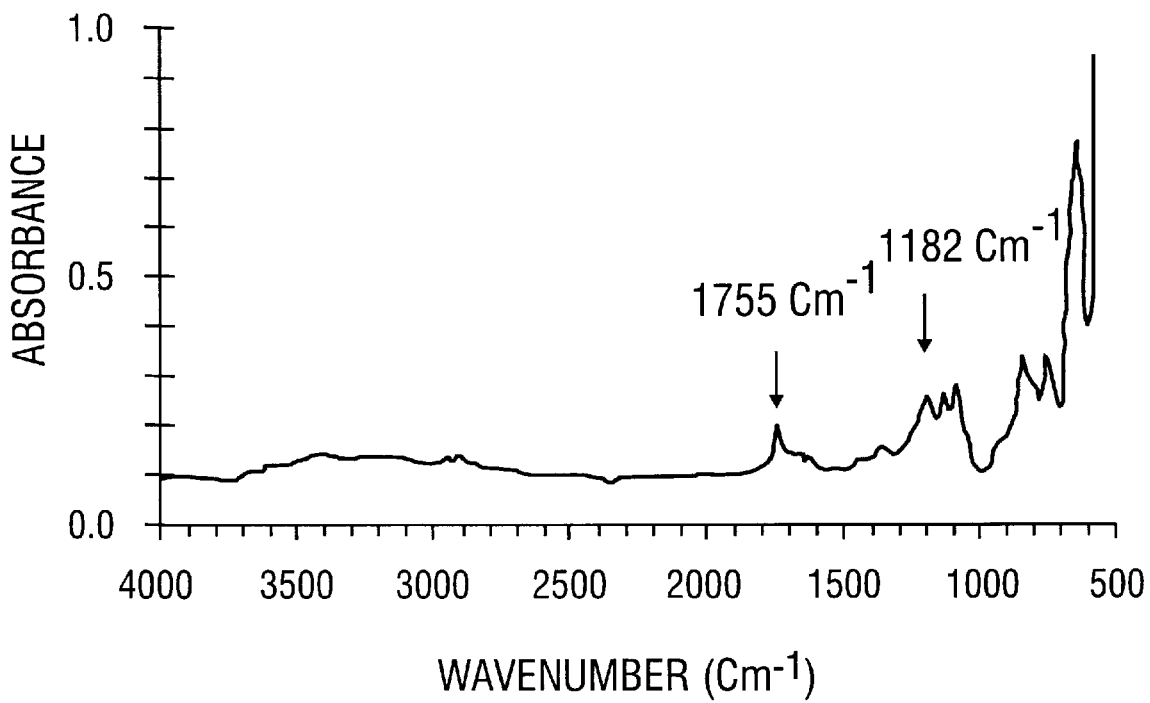
FIG. 5 shows an FTIR spectrum for PLA.
Figure 6:
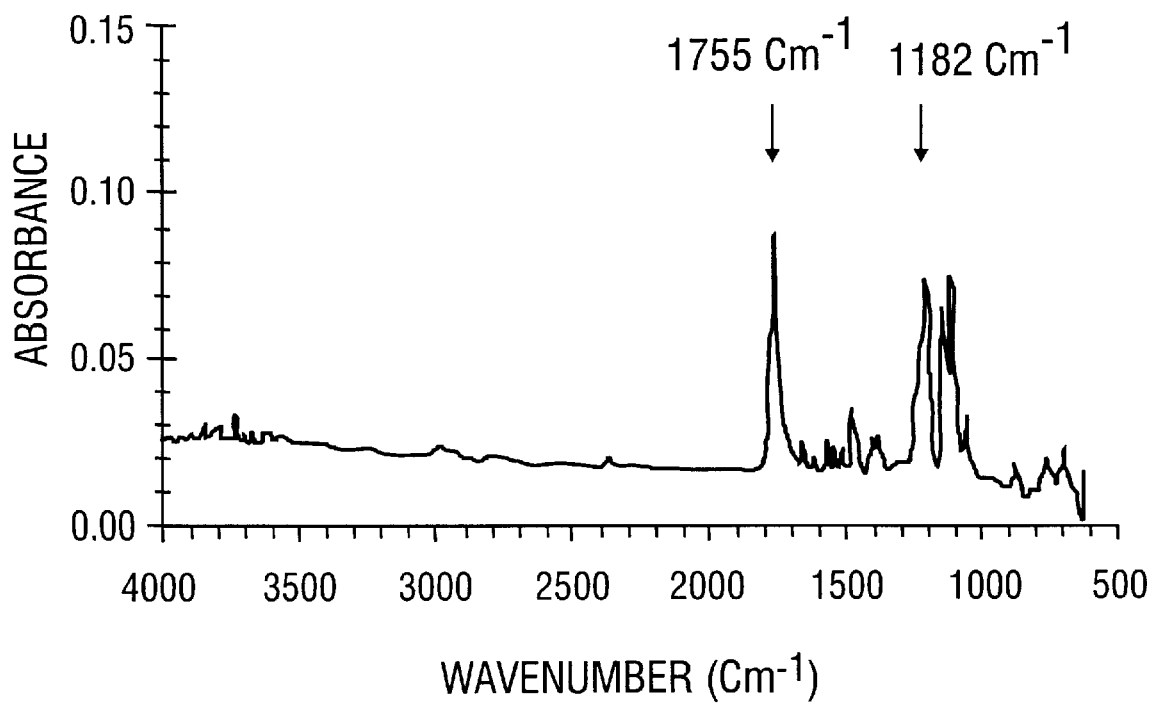
FIG. 6 shows an FTIR spectrum for PVC coated with PLA.

Longevity Testing: The FTIR spectrum in FIG. 1 is typical for uncoated PVC. Characteristic absorption peaks, due to the plasticizer, are located at 1722 cm$^{-1}$ and 956 cm$^{-1}$. The polylactic acid, which was used for coating the PVC, has characteristic absorption peaks at 1755 cm$^{-1}$ and 1182 cm$^{-1}$, as indicated by the spectrum in FIG. 5. After the PVC was coated with PLA, a FTIR spectrum was taken to understand how the PLA coating would appear on the PVC. The spectrum of coated PVC illustrated that the polylactic acid masks the absorption peaks of PVC at 1722 cm$^{-1}$ and 956 cm$^{-1}$. Hence, only the absorption peaks of PLA (1755 cm$^{-1}$ and 1182 cm$^{-1}$) are visible in FIG. 6. Although three different molecular weights of PLA were used, the initial spectra of the coatings were similar.

Figure 7:
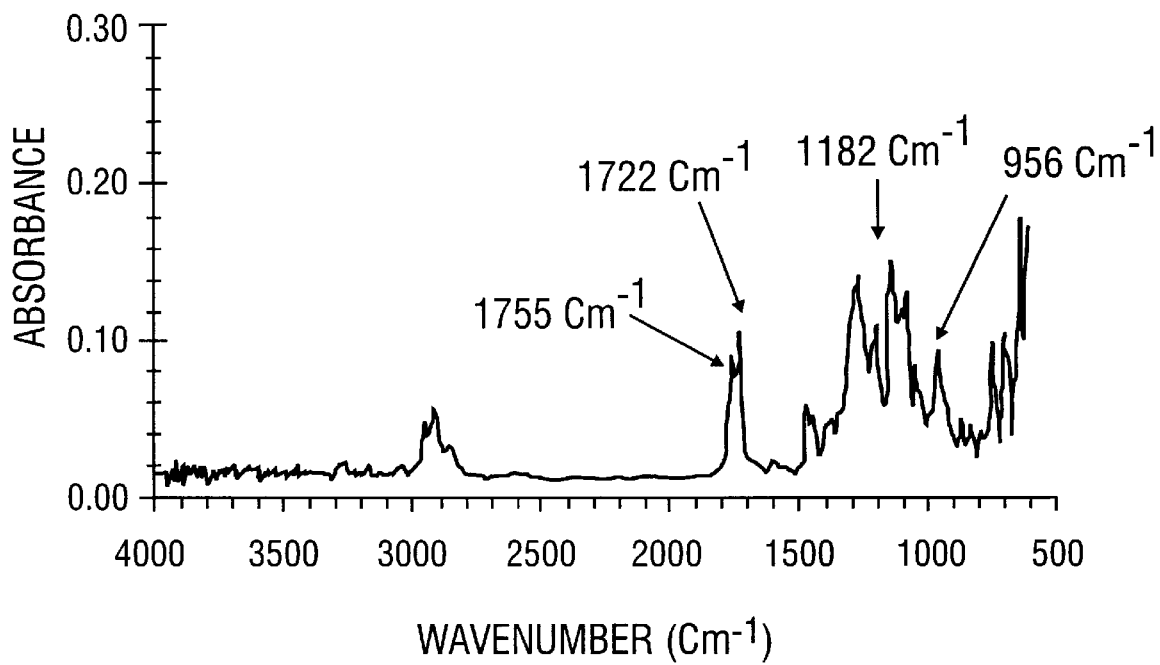
FIG. 7 shows an FTIR spectrum for PVC coated with PLA having a molecular weight of about 2,000, after partial dissipation in water for 56 hours.
Figure 8:
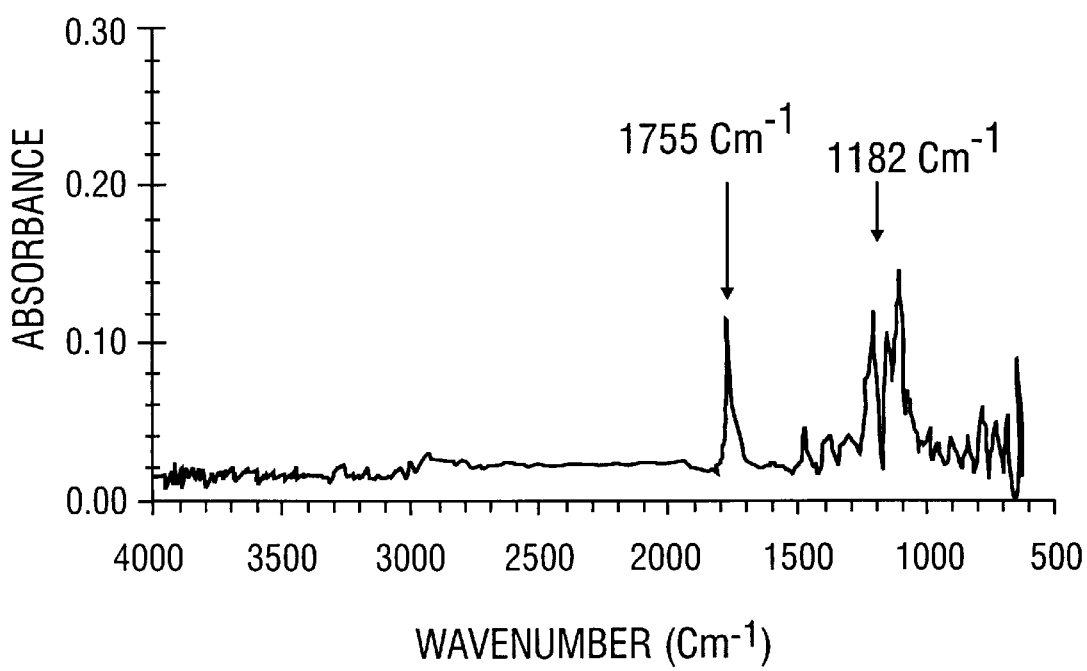
FIG. 8 shows an FTIR spectrum of PVC coated with PLA having a molecular weight of about 300,00, after partial dissipation in water over 56 hours.

The longevity of the coatings was determined by placing the different molecular weight samples in a buffer solution for varying increments of time. After each time interval a spectrum was taken of the sample to determine if there was evidence of degradation. The lower molecular weight samples did indicate hydrolysis of the PLA coating after extended periods in the buffer solution. This is illustrated by FIG. 7, a spectrum taken of 2,000 M.W. PLA after 56 hr in buffer solution. The absorption peaks of PLA (1755 cm$^{-1}$ and 1182 cm$^{-1}$) have decreased, while the PVC peaks (1722 cm$^{-1}$ and 956 cm$^{-1}$) have intensified. The higher molecular weight samples indicate that there was insufficient degradation during a similar time period to expose the underlaying PVC. This is illustrated in FIG. 8, a spectrum of 300,000 M.W. PLA after 56 hr, in which the PLA peaks (1755 cm$^{-1}$ and 1182 cm$^{-1}$) are still very intense. There is little or nothing of the PVC peaks at 1722 cm$^{-1}$ and 956 cm$^{-1}$ (compare FIG. 8 with FIG. 5).

Figure 9:
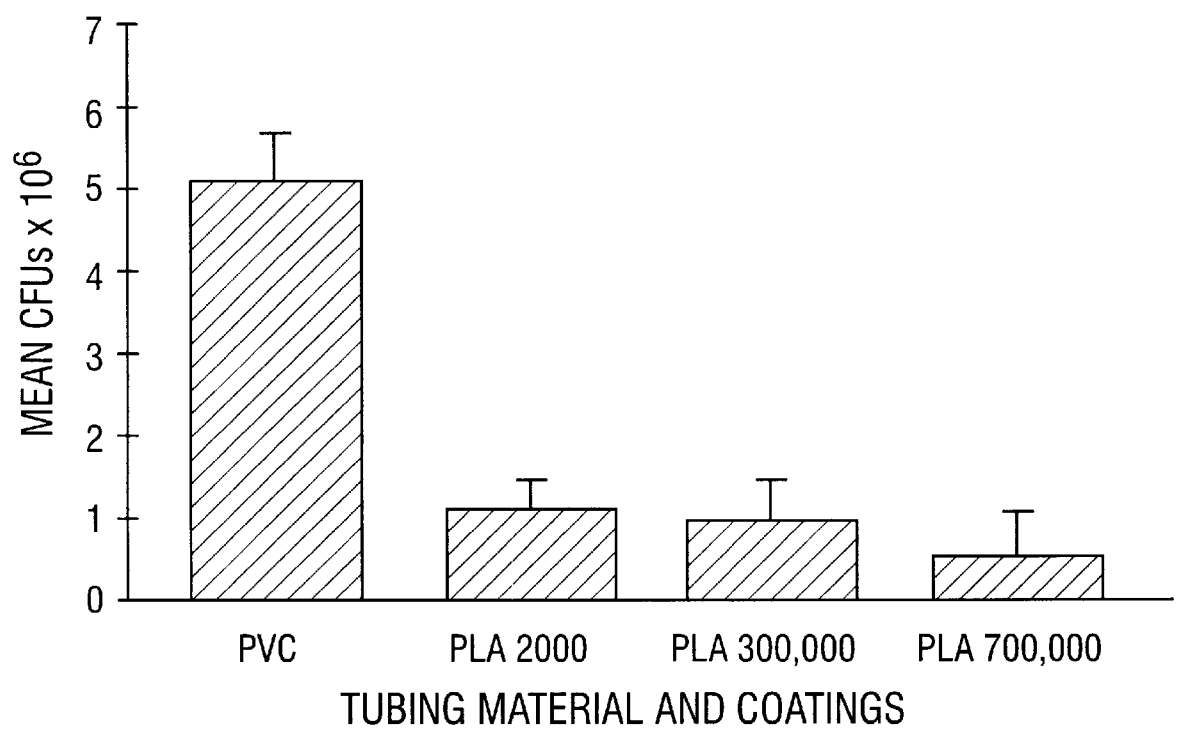
FIG. 9 shows the mean colony forming units formed for PVC or PVC coated with various PLA molecules.
Figure 10A:
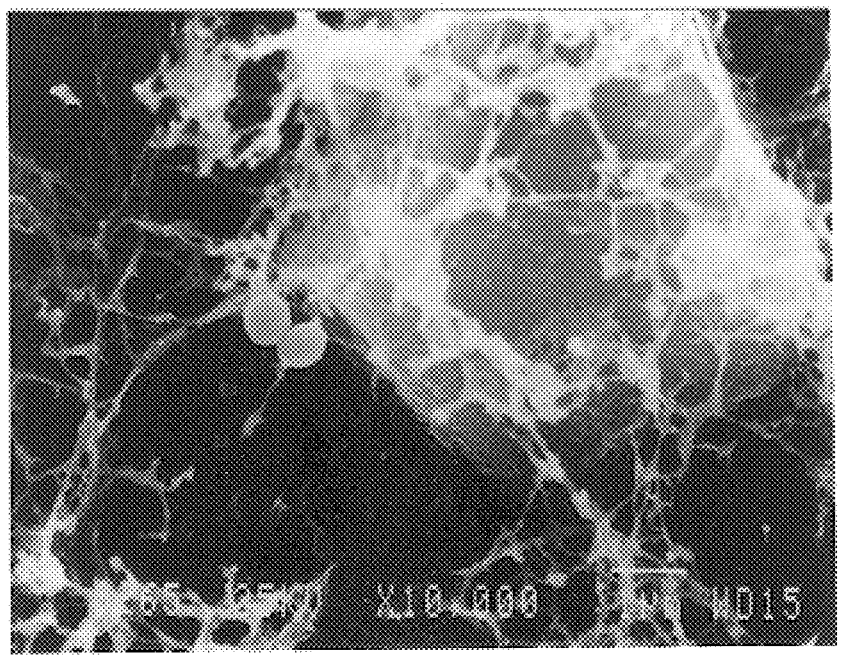
FIGS. 10A, 10B, 10C and 10D respectively show SEM of biofilm formation on PVC (10A), PVC coated with 2,000 molecular weight PLA (10B), PVC coated with 300,000 molecular weight PLA (10C), and PVC coated with 700,000 molecular weight PLA (10D).
Figure 10B:
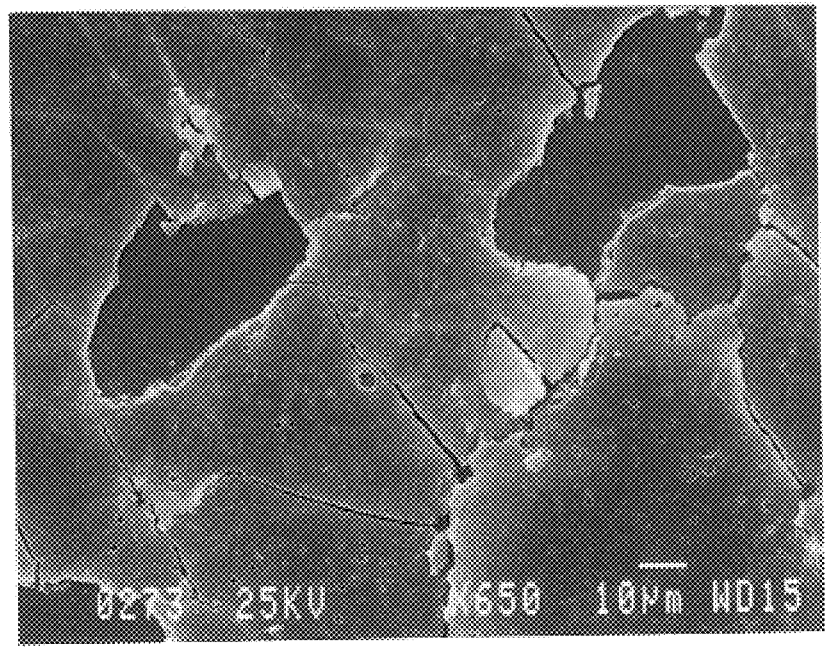
Figure 10C:
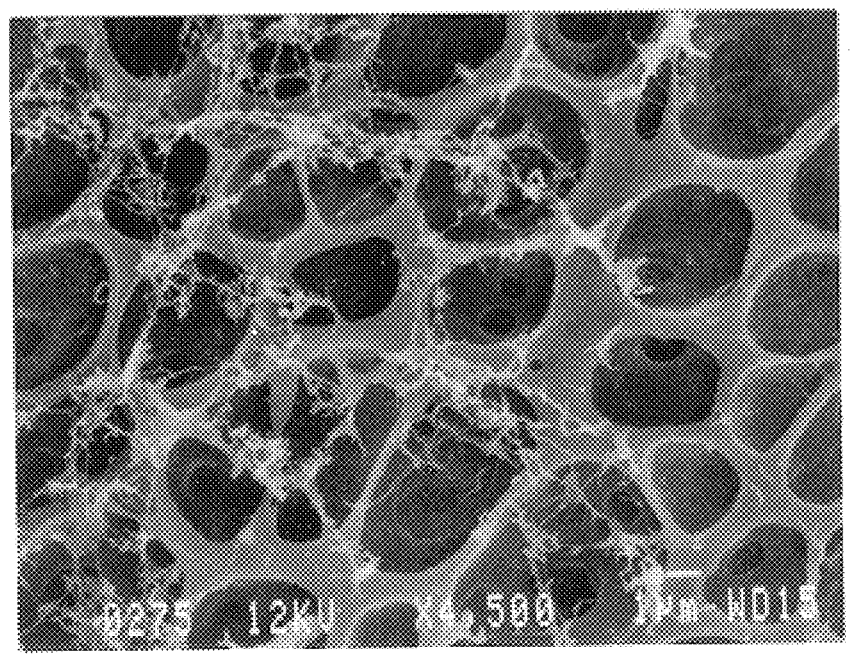
Figure 10D:
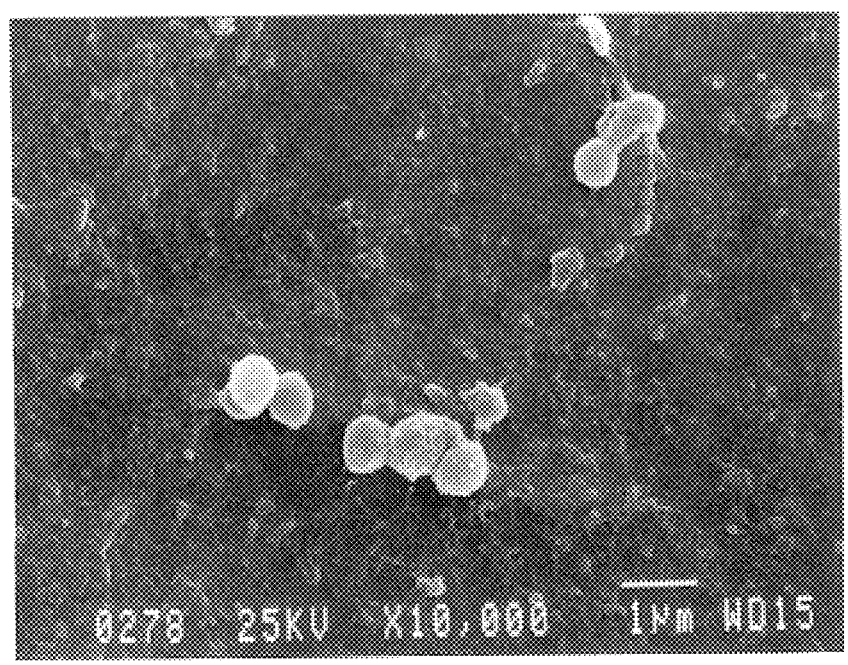

Bacteriological Testing: The bacterial resistance of the PVC coating was analyzed by colony counts and SEM examination. As indicated in FIG. 9, all three molecular weights of PLA had an inhibitory effect on bacterial colonization. The uncoated PVC showed significantly higher colony formation. The results also show an inversely proportional relationship between PLA molecular weight and the number of colony forming units (CFU) of *S. epidermidis*. As the molecular weight increased the CFUs decreased after 6 days of exposure.

SEM examination after 6 days exposure are shown in FIG. 10A, FIG. 10B, FIG. 10C and FIG. 10D. The 2,000 M.W. PLA coated PVC sample showed neither biofilm attachment nor colony growth (see FIG. 10B). The 300,000 M.W. sample did have biofilm formation but there was no significant colony formation (see FIG. 10C). The 700,000 M.W. sample also did not exhibit either colony growth nor biofilm formation, however, isolated bacteria were observed attached to the surface (see FIG. 10D). These organisms were relatively numerous after 3 days but sparse after 6 days and appeared to be atypical in morphology. The SEM photomicrographs also indicated that both the 2,000 M.W. and the 700,000 M.W. PLA coatings were still intact. However, the 300,000 M.W. PLA coating had a honeycomb-like porosity.

After analyzing the data from the longevity testing, it is clear that the PLA did hydrolyze after extended periods in aqueous solution. It is also evident that the rate of degradation is dependent on the molecular weight of PLA. The lower molecular weight PLA had a faster rate of degradation, in comparison to the higher molecular weight versions. The SEM photomicrographs suggest that there are two possible mechanisms for degradation. As seen for 2,000 M.W. and 700,000 M.W., the PLA appears to have degraded in a surface - down mechanism. In this mode, degradation occurs first at the surface and then gradually proceeds to the bottom layers. In the 300,000 M.W. material, a honeycomb porous structure indicates degradation from within the coating.

In doing the bacteriological analysis it was noted that all three of the PLA molecular weights had an anti-bacterial effect. However, there is some evidence that each molecular weight had a slightly different degree of effect. For example, the 700,000 M.W. coating did allow for isolated growth, but the morphology of the bacteria was abnormal. The abnormality could be a cytotoxic response to the lactic acid hydrolysis product of PLA. Hence, there may be more than one mechanism causing the antibacterial effect. Gradual PLA degradation can remove bacteria attached to the coating. It is also possible that a slow release of lactic acid to reduce the local pH may also be of significance. As the PLA hydrolyzes and forms lactic acid, acidic conditions are created at the surface and could further inhibit bacterial colonization and growth.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Dankert, Hogt and Feijen, "Biomedical polymers: bacterial adhesion, colonization and infection," *In: CRC Critical Reviews in Biocompatibility*, 2:219–301, 1986.

Sheu, Hoffman and Feijen, "A glow discharge treatment to immobilize poly(ethylene oxide)/poly(propylene oxide) surfactants for wettable and non-fouling biomaterials," *J Adhesion Sci. Technol.*, 6:995–1009, 1992.

van Wachen, Beugeling, Feijen, Eetmers and van Aken, "Interaction of cultured human endothelial cells with polymeric surfaces of different wettabilities," *Biomaterials*, 6:403–408, 1985.

What is claimed is:

1. A catheter or endotracheal tube device comprising a surface having a coating consisting essentially of a polymer soluble in or hydrolyzable by water, wherein said coating dissipates in an aqueous medium such that bacteria, fungi or biomolecules adhering to the coated surface are continually removed for at least six days.

2. The device of claim 1 where the dissipation is dissolution or hydrolysis.

3. The device of claim 1 defined further as comprising a polyvinylchloride surface.

4. The device of claim 1 defined further as comprising a surface of plastic, an elastomer, metal, or a composite thereof.

5. The device of claim 1 where the polymer is noncovalently attached and is soluble in water.

6. The device of claim 5 where the polymer is polyvinylalcohol, a soluble cellulose derivative, polyethylene oxide, polyvinlypyrolidone or polyethylene glycol.

7. The device of claim 1 where the polymer is covalently or noncovalently attached and is hydrolyzable by water.

8. The device of claim 7 where the polymer is a polyester or a polyanhydride.

9. The device of claim 1 where the polymer is hydrolyzable by water.

10. The device of claim 9 where the polymer is polylactide, polyglycolide, a polyanhydride, or a polylactide/polyglycolide copolymer.

11. The device of claim 1 wherein bacteria are Staphlococci.

12. The device of claim 1 wherein the fungus is a yeast.

13. The device of claim 12 wherein the yeast are Candida.

14. The device of claim 1 where the biomolecule is a protein or lipid.

15. A catheter having a surface at least partially coated with a coating consisting essentially of noncovalently adhering polymer which dissipates in an aqueous medium such that accumulation of adherent bacteria, fungi or biomolecules is inhibited.

* * * * *